(12) United States Patent
Soh et al.

(10) Patent No.: US 7,164,013 B2
(45) Date of Patent: Jan. 16, 2007

(54) HYPERACTIVE LIGHT SIGNAL RELATED MOLECULE OF HFR1-ΔN105 AND TRANSGENIC PLANT THEREOF

(75) Inventors: Moon-Soo Soh, Kwangju (KR); Pill-Soon Song, Kwangju (KR); Ki-Young Yang, Kwangju (KR)

(73) Assignee: Korea Kumho Petrochemical Co., Ltd., Seoul (KR)

( * ) Notice: Subject to any disclaimer, the term of this patent is extended or adjusted under 35 U.S.C. 154(b) by 539 days.

(21) Appl. No.: 10/641,100

(22) Filed: Aug. 15, 2003

(65) Prior Publication Data

US 2005/0039225 A1    Feb. 17, 2005

(51) Int. Cl.
  *C12N 15/29*    (2006.01)
  *C12N 15/52*    (2006.01)
(52) U.S. Cl. .............. 536/23.6; 536/23.1; 536/23.2
(58) Field of Classification Search .......... 536/23.1, 536/23.2, 23.6; 435/320.1; 800/290, 298, 800/306, 317, 320
  See application file for complete search history.

(56) References Cited

OTHER PUBLICATIONS

Thierry Desnos et al.: *FHY1: a phytochrome A-specific signal transducer*, Genes & Development 15:2980-2990, 2001.
Albrecht G. von Arnim et al.: *Light Inactivation of Arabidopsis Photomorphogenic Repressor COP1 Involves a Cell-Specific Regulation of Its Nucleocytoplasmic Partitioning*, CELL, vol. 79, 1035-1045, Dec. 16, 1994.
Christian Fankhauser et al.: *RSF1, an Arabidopsis Locus Implicated in Phytochrome A Signaling*; Plant Physiology, Sep. 2000, vol. 124, pp. 39-45.
Enamul Huq, et al.: *PIF4, a phytochrome-interacting bHLH factor, functions as a negative regulator of phytochrome B signaling in Arabidopsis*; The EMBO Journal, vol. 21, No. 10, pp. 2441-2450, 2002.
Ference Nagy et al.: *Phytochromes Control Photomorphogeneis by Differentially Regulated, Interacting Signaling Pathways in Higher Plants*; Annu. Rev. Plant Biol., 53:329-355, 2002.
G. C. Whitelam, et al.: *Roles of different phytochromes in Arabidopsis photomorphogeneis*; Plant, Cell and Environment, 20:752-758 (1997).
Yoshiharu Y. Yamamoto et al.: *CIP4, A New COP1 Target, Is a Nucleus-Localized Positive Regulator of Arabidopsis Photomorphogenesis*; The Plant Cell, vol. 13, 399-411, 2001.
Jason W. Reed et al.: *Phytochrome A and Phytochrome B Have Overlapping but Distinct Functions in Arabidopis Development*; Plant Physiol. 104: 1139-1149, 1994.
Young-Mi Kim et al.; *HFR1, a phytochrome A-signalling component, acts in a separate pathway from HY5, downstream of COP1 in Arabidopsis thaliana*; The Plant Journal 30(6): 711-719, 2002.
Craig D. Fairchild et al.: *HFR1 encodes an atypical bHLH protein that acts in phytochrome A signal transduction*; Genes & Development 14:2377-2391, 2000.

*Primary Examiner*—Russell P. Kallis
(74) *Attorney, Agent, or Firm*—Kenyon & Kenyon LLP

(57) ABSTRACT

This invention is about the functionally hyperactive light signal related molecule, HFR1-ΔN105, of which the nucleic acids that encode N-terminal 105 amino acid residues were deleted. HFR1 as a bHLH transcription factor functions in a subset of phytochrome A signaling cascade and it was reported to be regulated negatively by COP1. Experiments with a HFR1-ΔN105 overexpressing plant revealed that the deletion of N-terminal amino acids makes the HFR1 more active in photomorphogenic development such as germination and de-etiolation. In addition, the transgenic plants showed hypersensitive photo-responses in the inhibition of hypocotyl elongation, dependently on another positive element of light signaling, a bZIP protein, HY5. The end-of-day far-red light response and petiole elongation were suppressed in the HFR1-ΔN105 overexpressing plants. These results suggest that N-terminal region of HFR1 negatively regulate HFR1 function and that HFR1-ΔN105 is hyperactive.

2 Claims, 7 Drawing Sheets

HYPERACTIVE LIGHT SIGNAL RELATED MOLECULE OF HFR1-ΔN105 AND TRANSGENIC PLANT THEREOF

FIELD OF THE INVENTION

This invention relates to a functionally hyperactive light signal related molecule, HFR1-ΔN105, of which the nucleic acids that encode N-terminal 105 amino acid residues are deleted. The HFR1 as a bHLH transcription factor has a function of the subset of phytochrome A signaling cascade and its function is negatively regulated by COP1. Experiments with transgenic plants show that N-terminal residue deletion makes the HFR1 more active. The present invention also provides the methods for generating transgenic higher plants transformed with the said nucleic acid molecule to enhance the shade avoidance of economically important crop plants.

BACKGROUND OF THE INVENTION

Light affects various aspects of growth and development in higher plants throughout their life cycles, from germination to flowering (Fankhauser and Chory, 1997). Seedlings grown in the dark undergo skotomorphogenesis, characterized by elongated hypocotyls, yellow and closed cotyledons. In response to light, seedlings undergo photomorphogenesis; hypocotyls cease elongating, cotyledons become green and unfolded, and the seedlings become photosynthesis competent.

A number of photoreceptors controlling light-dependent development, including red (R) and far-red (FR) light absorbing phytochromes, blue light receptors, cryptochromes, and phototropins have been characterized (Furuya, 1993; Lin, 2000). Among these, the phytochromes are the best characterized. Phytochromes exist as two photo-interconvertible forms, Pr (R light-absorbing phytochrome) and Pfr (FR light-absorbing phytochrome), depending on light conditions (Butler et al., 1959). In higher plants, phytochrome apoproteins are encoded by a small gene family, such as PHYA-E in *Arabidopsis* (Sharrock and Quail, 1989). Mutational and transgenic approaches have revealed that individual phytochromes have overlapping but distinct functions (Reed et al., 1994; Quail et al., 1995; Furuya and Schäfer, 1996; Whitelam and Devlin, 1997). In particular, phyA is a primary photoreceptor for FR-high irradiance response (HIR) and very low fluence response (VLFR), whereas phyB is a primary photoreceptor for R-HIR and R-low fluence response (LFR).

The downstream components of phytochrome signaling have been extensively characterized. Light-dependent post-translational modifications and subcellular localization of phytochromes have also been implicated to play a role in phytochrome downstream signaling (Lapko et al., 1997; Yeh and Lagarias, 1998; Kircher et al., 1999; Yamaguchi et al., 1999; Kim et al., 2002b). Several phytochrome-interacting molecules have been identified; implying that phytochrome may utilize multiple interacting partners to induced various photoresponses (Quail, 2002b).

Mutant screening using light-dependent seedling development has been fruitful to reveal a number of phytochrome-signaling components, including photoreceptors (Neff et al., 2000). One class of mutants includes the ones that exhibit altered photo-responses under different light conditions, defining light-dependent positive and negative regulators. Several of these are transcription factors, including two basic helix-loop-helix (bHLH) proteins, HFR1 and PIF4 (Fairchild et al., 2000; Fankhauser and Chory, 2000; Soh et al., 2000; Huq and Quail, 2002), a bZIP protein, HY5 (Oyama et al., 1997), and a MYB protein, LAF1 (Ballesteros et al., 2001), that have been shown to regulate not only distinct but overlapping subsets of photoresponses. EID1 and SPA1, phyA-dependent negative regulators, have been implicated to control protein stability in the nucleus (Hoecker et al., 1999; Dieterle et al., 2001; Hoecker and Quail, 2001). The other class of mutants revealed a group of repressors of photomorphogenesis, COP/DET/FUS. The cop/det/fus mutations confer photomorphogenic development even in the absence of light, including shortened hypocotyls, expanded cotyledons, and increased expression of light-inducible genes (Chory et al., 1989; Wei and Deng, 1996). Recent studies proposed that DET1, a nuclear protein, regulates gene expression via chromatin remodeling, which could control the accessibility of a promoter to specific transcription factors, for example (Benvenuto et al., 2002; Schroeder et al., 2002). COP1 encodes a RING-finger protein with WD 40 repeats whose nuclear localization is negatively regulated by light (Deng et al., 1992; von Arnim and Deng, 1994). In darkness, COP1 interacts with, and down-regulates several transcription factors that act as positive components in light signaling (Ang et al., 1998; Hardtke et al., 2000; Osterlund et al., 2000; Yamamoto et al., 1998, 2000). Other cop/det/fus loci encode an ubiquitin-conjugating enzyme or components of the COP9 signalosome complex, which was proposed to function in the proteasome-mediated protein degradation (Suzuki et al., 2002; Serino et al., 2003). Together, these findings led to the hypothesis that the primary mode of phytochrome signaling for seedling development involves post-translational regulation on the nuclear transcription (Nagy and Schäfer, 2002). Despite extensive list of phytochrome signaling components, the molecular mechanisms by which these components mediate phytochrome downstream signaling mechanism are still poorly understood (Nagy and Schäfer, 2002). In particular, it is notable that no molecular components have been identified to mediate phytochrome-dependent germination.

Previously, HFR1, a bHLH protein was shown to be required for a subset of phyA-dependent responses and act downstream of COP1 (Fairchild et al., 2000; Fankhauser and Chory, 2000; Soh et al., 2000; Kim et al., 2002b). Here we used a transgenic approach to further investigate the role of HFR1 in light signaling.

SUMMARY OF THE INVENTION

The present invention relates to nucleic acid molecules encoding mutant HFR1, a basic helix-loop-helix protein of which N-terminal 105 amino acids is deleted. Such nucleic acid molecules preferentially encode a protein with the amino acid sequence as given in SEQ ID NO: 2. The mutant HFR1 confers constitutive photoresponses in a subset of photomorphogenic development and hypersensitivity in the response of higher plants to light.

Also, the invention includes an uninterrupted gene sequence encoding the HFR1-ΔN105, a nucleic acid fragment that can be directly ligated into recombinant DNA constructs, and the HFR1-ΔN105 expression vectors that can be readily used to transform cells of higher plants.

The invention provided transgenic higher plants that are readily accessible to the *Agrobacterium*-mediated transformation. Overexpression of the HFR1-ΔN105 gene results in hypersensitive photoresponses. These phenotypic traits can be exploited in a way that higher plants of interest harboring the HFR1-ΔN105 gene exhibit decreased shade avoidance syndrome, a very important commercial trait in horticulture and agriculture.

Therefore, the present invention provides: 1. Nucleic acid molecules encoding a polypeptide of a modified mutant HFR1, a basic helix-loop-helix protein of which N-terminal 105 amino acids is deleted, comprising a nucleotide sequence as given in SEQ ID NO: 1.

DETAILED DESCRIPTION OF THE INVENTION

Phytochromes are the best-characterized photoreceptor that regulates diverse aspects of growth and development in higher plants. Upon irradiation, it exhibits interconvertible photo-conversion between biologically inactive Pr (red absorbing phytochrome) form and biologically active Pfr (far-red absorbing phytochrome) form that enables it to act as a molecular light switch (Butler et al., 1959). The activated Pfr triggers downstream signaling that result in diverse photo-responses.

In *Arabidopsiss*, phytochrome apoproteins are encoded by a small gene family, PHYA-E (Sharrock and Quail, 1989). Mutational and transgenic approaches have revealed that individual phytochromes have overlapping but distinct functions (Reed et al., 1994; Quail et al., 1995; Furuya and Schäfer, 1996; Whitelam and Devlin, 1997). In particular, phyA is a primary photoreceptor for FR-high irradiance response (HIR) and very low fluence response (VLFR), whereas phyB is a primary photoreceptor for R-HIR and R-low fluence response (LFR).

The HFR1 is revealed as a basic helix-loop-helix protein that is required in a subset of phytochrome A (phyA)-mediated photo-responses in *Arabidopsis* (Fairchild et al., 2000; Fankhauser et al., 2000; Soh et al., 2000).

Figure 1:
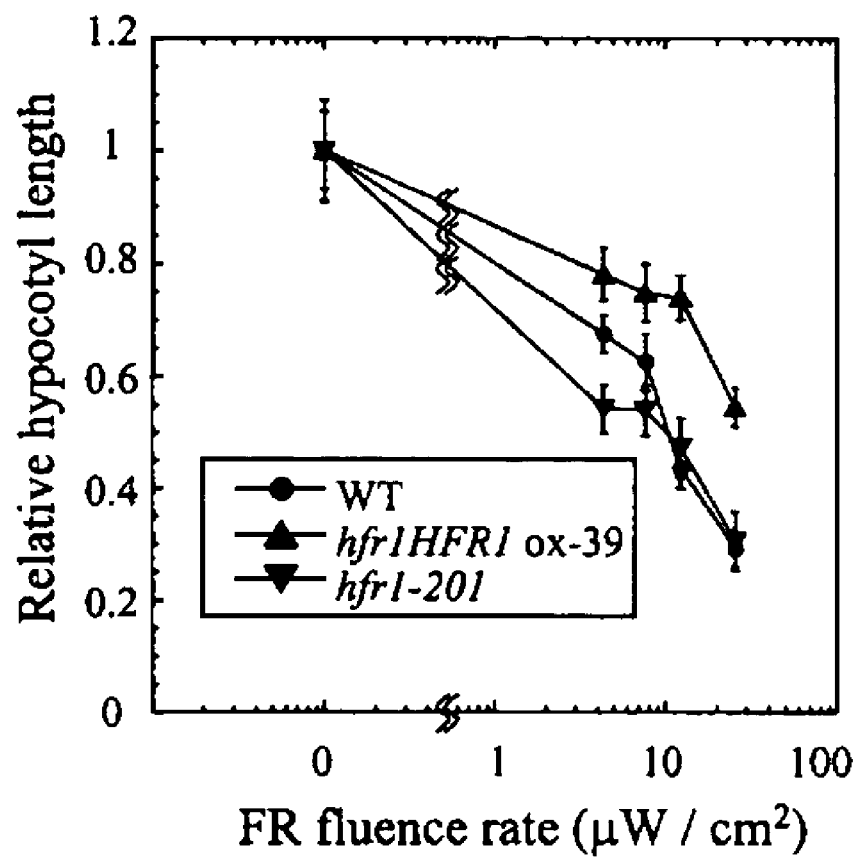
FIG. 1. Fluence rate responses of inhibition of hypocotyl elongation under FR light. The data are expressed as average relative hypocotyl length from at least 20 seedlings, normalized to their respective hypocotyl length in darkness±standard deviation. The error bars indicate standard deviations. WT, wild type.
Figure 2:
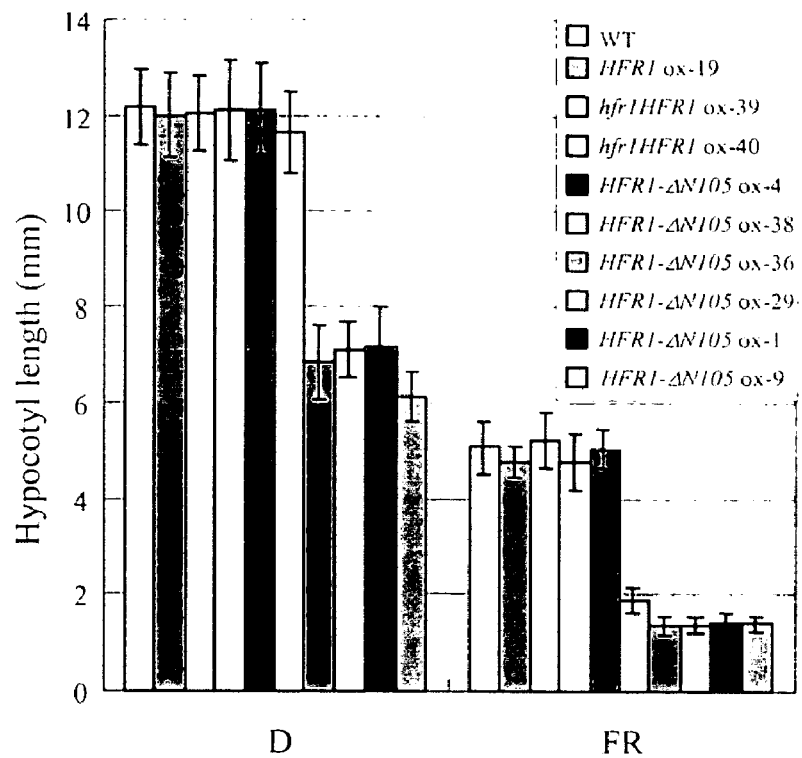
FIG. 2. Photomorphogenic phenotypes of HFR1-ΔN105 overexpressing transgenic *Arabidopsis*.
(A) Hypocotyl elongation phenotypes in wild type and transgenic plants overexpressing full-length HFR1 or HFR1-ΔN105. The seedlings were grown for 4 days under FR light (21 μW/cm$^2$) or in darkness. Each measurement was performed on at least 20 seedlings. The data are expressed as average hypocotyl length±standard deviation. WT, wild type.
(B) RNA gel blot analysis of wild type and transgenic plants overexpressing full-length HFR1 or HFR1-ΔN105. Total RNA (10 μg) was loaded and subject to RNA gel blot analysis. The blot was hybridized with a $^{32}$P-labeled HFR1-ΔN105 probe. The 18S rRNA was used as a loading control. The signals were visualized with a PhosphoImager (Fuji, FLA2000). WT, wild type.
Figure 2:
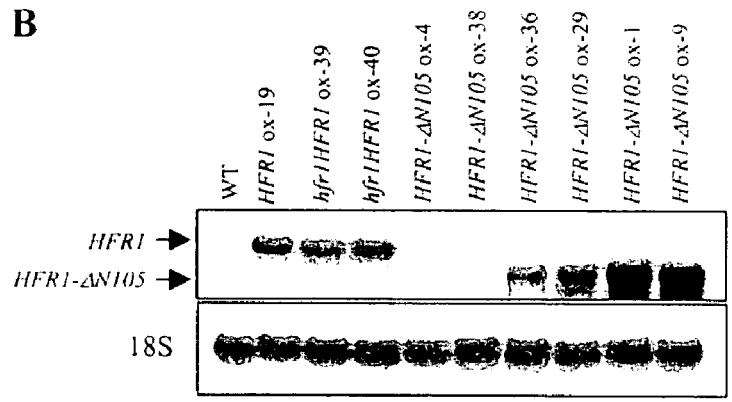

To further investigate the functions of HFR1 in light signaling, we stably introduced HFR1 into mutant hfr1-201 and wild type *Arabidopsis*. The hypocotyl phenotype of the mutant hfr1-201 was complemented by the HFR1 overexpression (FIGS. 1 and 2A). However, the wild type plant overexpressing HFR1 did not show any phenotypic alterations. It suggests that the full-length HFR1 is not a limiting factor for the photo-responses and the negative control mechanism may be involved. To test this possibility, we generated two modified HFR1 genes: HFR1-ΔN105, which lacks the DNA sequence encoding 105 N-terminal end amino acids, and HFR1-ΔC45, which lacks the DNA sequence encoding 45 C-terminal end amino acids. These two modified HFR1s were stably introduced into *Arabidopsis*. While the transgenic plants overexpressing HFR1-ΔC45 did not exhibit any differences in the photo-responses (data not shown), the transgenic plants overexpressing HFR1-

Figure 3:
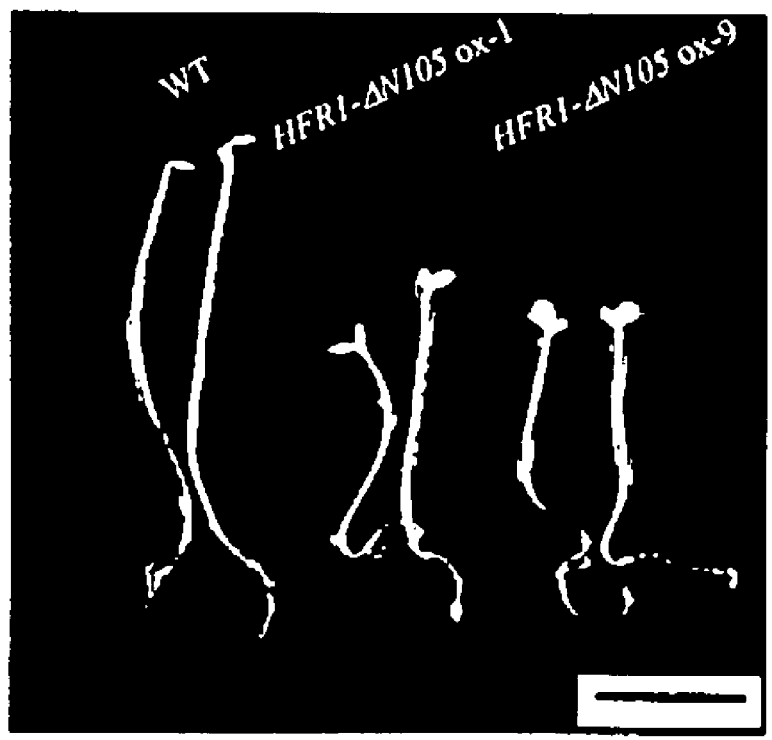
FIG. 3. Morphology of representative HFR1-ΔN105 overexpressing transgenic *Arabidopsis* seedlings. The seedlings were grown for 5 days in darkness. The scale bar is 5 mm. WT, wild type.

ΔN105 showed shortened hypocotyls under light and dark conditions (FIG. 2A). In addition, the HFR1-ΔN105 transgenic plants displayed cotyledon opening/expansion and apical hook opening in the dark (FIG. 3). The phenotypic severity of the transgenic lines appeared to correlate with the expression level of HFR1-ΔN105 transgene (FIG. 2B). But the HFR1-ΔN105 ox-36 line exhibited shortened hypocotyls in darkness, even though the expression level of the transgene was lower than that of the lines expressing full-length HFR1. This result indicates that the exaggerated photo-responses of the HFR1-ΔN105 transgenic lines may not be simply due to the higher expression level of the HFR1-ΔN105 transgene. Taken together, it is possible to suggest that the N-terminal region of HFR1 is negatively controlled and HFR1-ΔN105 is hyperactive conferring photomorphogenic development even in the absence of light.

Figure 4:
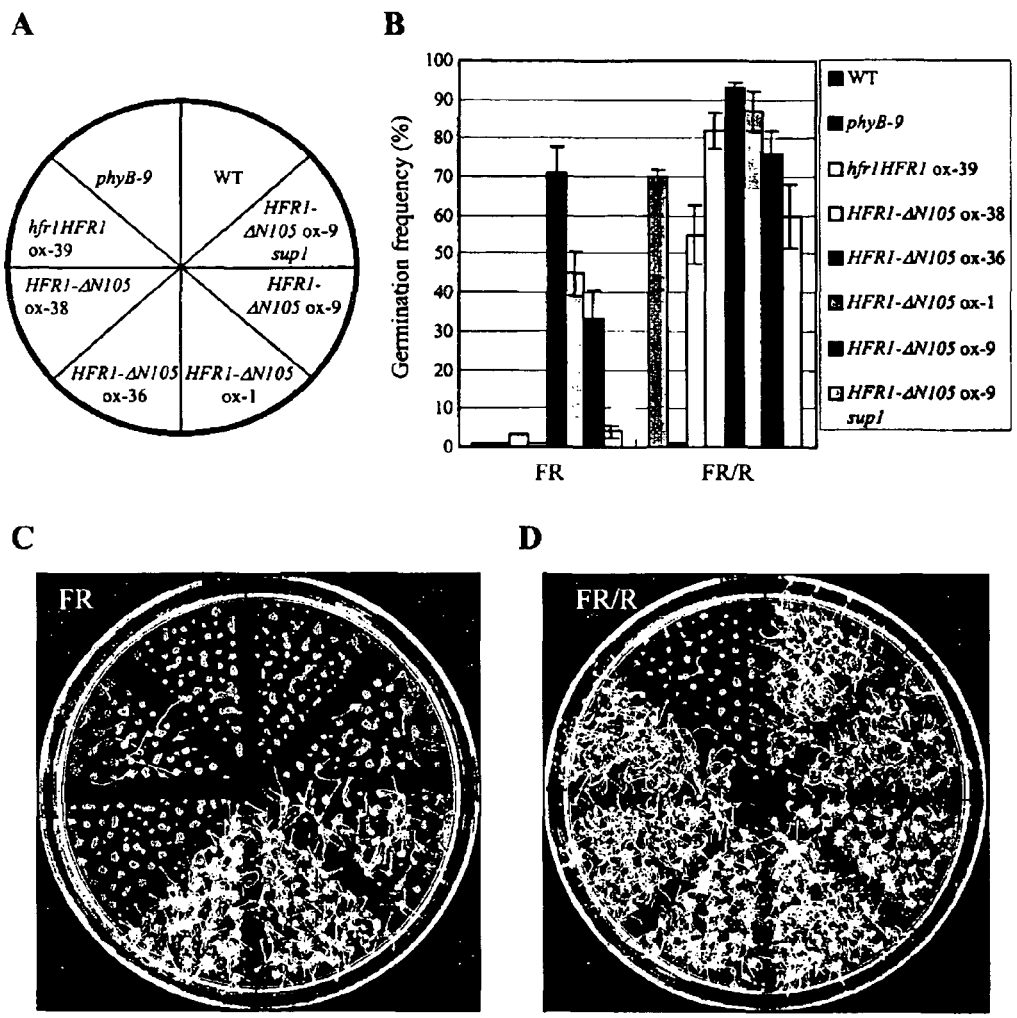
FIG. 4. Phytochrome-dependent germination response.
(A) Summary of seeds used in the germination experiment. WT, wild type.
(B) Germination frequencies of wild type (WT) or various transgenic plant lines overexpressing HFR1 or HFR1-ΔN105 seeds were measured. The seeds were treated with FR light (21 μW/cm$^2$) for 15 min just after imbibition and then transferred to darkness without or with exposure to R light (33 μW/cm$^2$) for 10 min. Seeds were then incubated in darkness for an additional 5 days. Each experiment was performed with at least 150 seeds. Similar results were obtained from three independent experiments.
(C) Representative plates from the germination experiments described in (B). The plates were given a pulse of FR light and kept in darkness.
(D) Representative plates from the germination experiments described in (B). The plates were given a pulse of R light after a pulse of FR light and then further kept in darkness.

Phytochromes mediate the induction of germination by light. Treatment with a pulse of FR light just after imbibition inhibits germination, whereas subsequent irradiation with R light results in phyB-mediated seed germination (Shinomura et al., 1996). Thus, the phyB mutant seeds do not germinate even after the treatment of R light. So far, except the photoreceptor itself, no mutations that mediate phytochrome-dependent seed germination have been identified. However, the seeds of HFR1-ΔN105 transgenic lines germinated after FR light treatment. It implies that the seeds are able to undergo light-independent germination (FIG. 4). The intragenic suppressor of HFR1-ΔN105 overexpressor (sup1) could restore the altered germination phenotype of HFR1-ΔN105 ox-9, further suggesting that the constitutive germination was due to the overexpression of HFR1-ΔN105. These results indicate that HFR1-ΔN105 affects phytochrome signaling that leads to germination.

Figure 5:
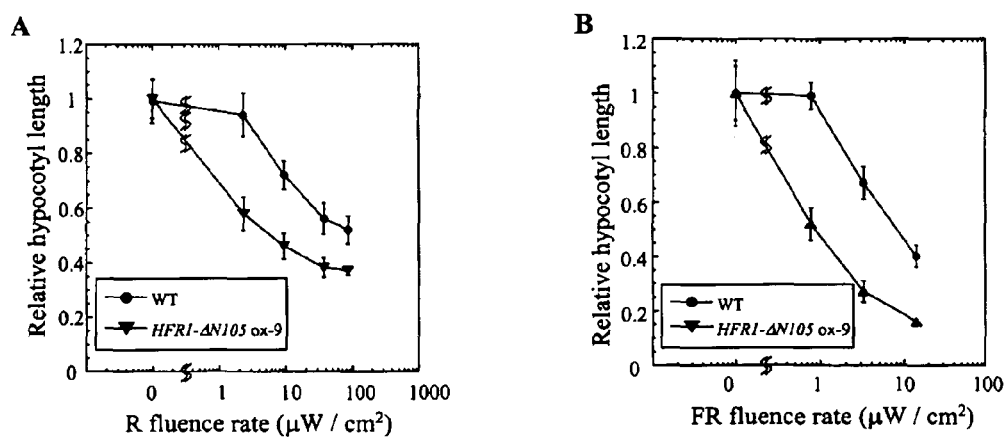
FIG. 5. Hypocotyl elongation responses of transgenic plants overexpressing HFR1-ΔN105 mutant.
(A) Fluence rate responses of inhibition of hypocotyl elongation under R light. The data are expressed as average relative hypocotyl length from at least 20 seedlings, normalized to their respective hypocotyl length in darkness±standard deviation. The error bars indicate standard deviations. WT, wild type.
(B) Fluence rate responses of inhibition of hypocotyl elongation under FR light. WT, wild type.

To examine the photo-responses of the HFR1-ΔN105 overexpressing plants in the inhibition of hypocotyl elongation in detail, we grew seedlings under various fluence rates of R or FR light. Compared to wild type, HFR1-ΔN105 transgenic plants were hypersensitive to both R and FR light (FIGS. 5A and B). Together with the phenotype showing shortened hypocotyls in darkness, these results imply that not only can HFR1-ΔN105 activate photo-responses independently of light conditions, but it can also act synergistically with other light-signaling components to inhibit hypocotyl elongation in the presence of light.

Figure 6:
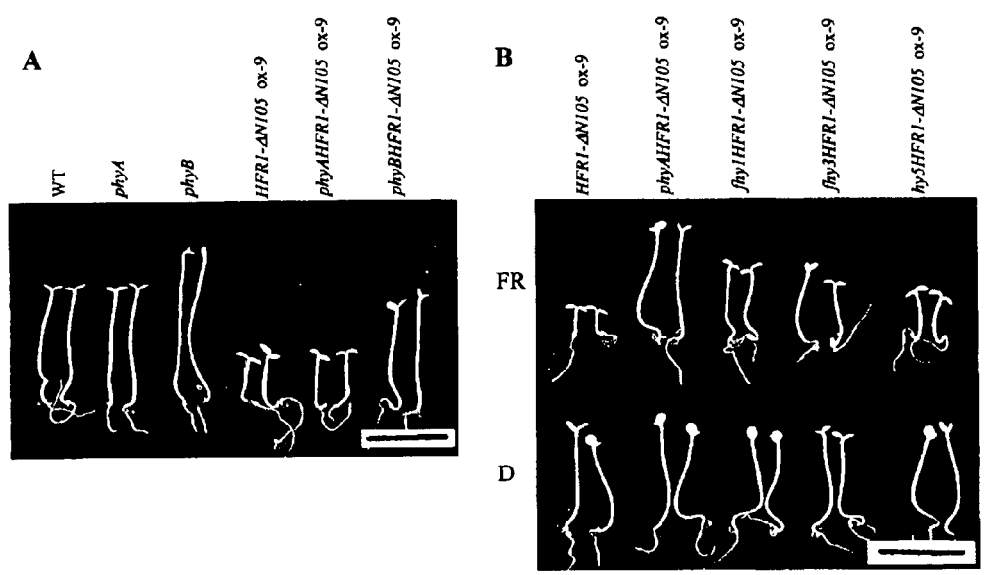
FIG. 6. Hypocotyl elongation responses of HFR1-ΔN105 ox double mutant.
(A) Representative seedlings of the wild type (WT), phyA-211, phyB-9, HFR1-ΔN105 α-9 and double mutants, grown under R light (33 μW/cm$^2$) for 4 days. The scale bar is 5 mm.
(B) Representative seedlings of the wild type (WT), phyA-211, fhy1-311, fhy3-311, hy5-221 and HFR1-ΔN105 ox-9 and double mutants, grown under FR light (14 μW/cm$^2$) (upper panel) or in darkness (lower panel) for 4 days. The scale bar is 5 mm.

In some cases, enhanced phyA signaling could lead to hypersensitivity to R light as well as FR light (Hoecker et al., 1998; Büche et al., 2000). To determine which photoreceptor mediates the hypersensitive photo-response of HFR1-ΔN105 transgenic plants, we constructed phyAHFR1-ΔN105 ox, and phyBHFR1-ΔN105 ox double mutants. As shown in FIGS. 6A and B, the enhanced photo-responses of HFR1-ΔN105 ox plants under FR light or R light were absent in plants on the phyA mutant or phyB mutant backgrounds, respectively. Thus, the enhanced photo-responses of HFR1-ΔN105 transgenic plants under FR or R light required functional phyA or phyB, respectively.

To examine the dependence of HFR1-ΔN105 on the downstream signaling components of phyA for its enhanced photo-responses, we generated double mutants of HFR1-ΔN105 transgenic lines and the mutants, fhy1 or fhy3, which are well known upstream components in phyA signaling. FHY1 and FHY3 have been shown to define a distinct signaling branch (Desnos et al., 2001; Okamoto et al., 2001; Wang and Deng, 2002). Our experiments showed that both FHY1 and FHY3 are necessary for the shortened hypocotyls exhibited by HFR1-ΔN105 transgenic plants (FIG. 6B). We also investigated the relationship between HFR1-ΔN105 and HY5, a bZIP transcription factor that plays a positive role in light signaling, in that HY5 and HFR1 additively inhibit hypocotyl elongation under FR light (Kim et al., 2002b). We found that the enhanced light responses of HFR1-ΔN105 overexpressing plants were decreased on the hy5 mutant background. In contrast, the hy5 mutation did not affect the shortened hypocotyl phenotype of HFR1-ΔN105 overexpressing plants in darkness. Thus, the results suggest that HFR1-ΔN105 may function cooperatively with HY5 to inhibit hypocotyl elongation in response to light.

Figure 7:
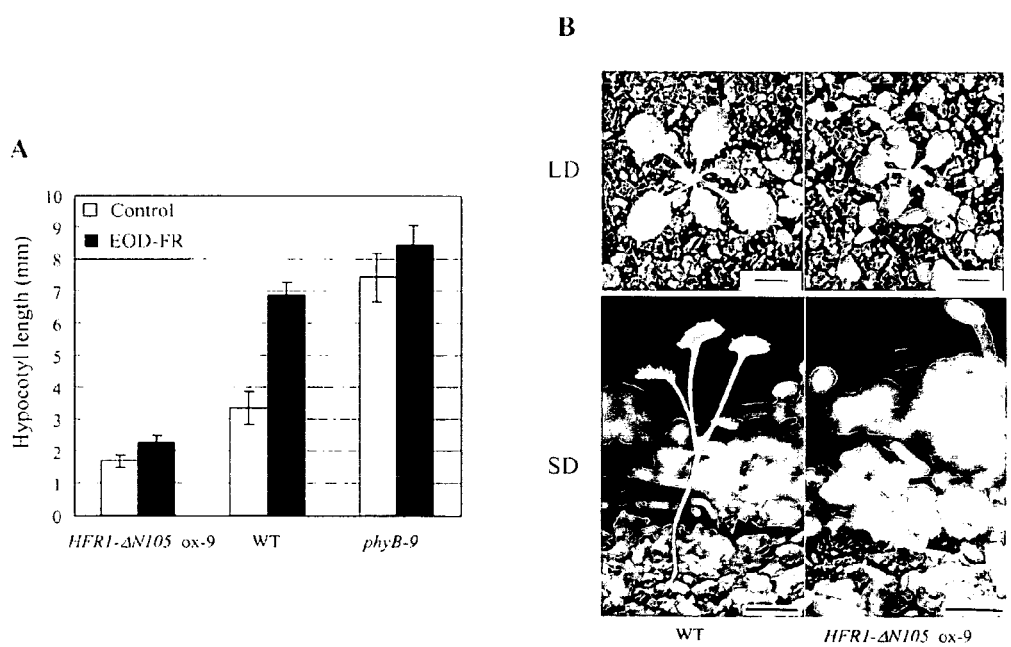
FIG. 7. Photo-responses of transgenic plants overexpressing HFR1-ΔN105 under white light.
(A) End-of-day (EOD) FR responses of wild type and transgenic plants. The average hypocotyl lengths±standard deviations are shown from at least 20 seedlings in each group. Hatched bars, no EOD-FR treatments; black bars, EOD-FR treatments. WT, wild type.
(B) Morphology in adult wild type (WT) and transgenic plants overexpressing HFR1-ΔN105. The plants were grown for 20 days under long day (16 hr L/8 hr D) or for 24 days under sort day (8 hr L/16 hr D) conditions. The scale bar is 5 mm.

In the case of plants grown under white (W) light, stable phytochromes, primarily phyB, mediate various light-responses, such as hypocotyl/petiole elongation (Whitelam and Devlin, 1997). To test whether HFR1-ΔN105 affects the low fluence response, which is primarily regulated by phyB, we examined end of day (EOD)-FR light response. While wild type seedlings exhibited longer hypocotyls under EOD-FR light conditions, as compared to control short day conditions, phyB mutant plants exhibit a constitutive EOD-FR light response. The overexpression of HFR1-ΔN105 significantly suppressed hypocotyl elongation in response to EOD-FR light treatment (FIG. 7A). The results indicate that HFR1-ΔN105 ox-9 is less sensitive to inactive phytochromes that would be formed by FR light treatment at the EOD.

In adult plants, petiole elongation was inhibited in HFR1-ΔN105 transgenic plants under both long-day and short-day conditions (FIG. 7B). This result indicates that HFR1-ΔN105 enhanced a subset of phytochrome signaling pathways in response to W light, including those that regulate hypocotyl and petiole elongation.

EXAMPLES

Plant Materials and Growth Conditions

The seeds of wild type (Col), phyB-9 and phyA-211 mutants lines were obtained from *Arabidopsis* Biological Resources Center (ABRC) (Columbus, Ohio). The fhy3-1 seed was kindly provided by Dr. Garry Whitelam (Leicester University, UK) and the hy5-221 seed was obtained from Dr. Xing-Wang Deng (Yale University, New Haven, Conn.). The fhy1-311 mutant was derived from our mutant screening with EMS-mutagenized seeds and was shown to be a null mutation (unpublished result). All mutants used are from Col background. Light conditions used were same as previously described (Soh et al., 2000). For measurement of hypocotyl lengths, seeds were surface sterilized for 5 min in commercial bleach and rinsed with sterile distilled water at least five times. Seeds were then sown onto MS medium containing 0.8% agar. After incubation at 4° C. for 3 days, the plates were placed in W light for 12 hours at 23° C. to improve germination and then transferred to the appropriate light conditions. Data were collected from 40% of the longest seedlings, to minimize variation in hypocotyl lengths among the seedlings as described previously (Soh et al., 1998). Germination tests were performed as described by Shinomura et al. (1996). Seeds were surface-sterilized and sown on aqueous medium containing 0.7% agar. Seeds were irradiated with FR light (21 $W/cm^2$) for 15 min and then kept in darkness with or without a single pulse of R light (33 $W/cm^2$) for 10 min. After 5 days, germination frequency was determined.

Enzymatic Treatments of DNA

DNA manipulations were carried out according to the standard procedures with some modifications whenever required. Restriction enzyme digestions were routinely done in 20 µl reaction volumes with an enzyme of 1–5 units per microgram DNA, and the mixtures were incubated at an appropriate temperature for 1–2 hours. Restriction enzyme digestion buffers used were those supplied by the manufacturer for each particular enzyme, unless specified otherwise. For ligation reactions, DNA fragments, either a digestion mixture or a PCR product, were first separated on 0.8–1.5% agarose gels, depending on the sizes of the DNA fragments of interest, and the desired DNA fragment was purified from the gel piece using either the GENECLEAN II Kit (BIO 101, Vista, USA) or the Gel Extraction Kit (Omega Biotek, Doraville, USA). Ligations were performed usually at the molar ratio of 1:1 to 1:3 in a 10 µl volume using the buffer supplied by the manufacturer, and the mixture was incubated at 13–16° C. for 10 minutes (for sticky-end ligations) or 30 minutes (for blunt-end ligations). T4 DNA ligase and its corresponding ligase buffer (NEB, Beverly, Mass., USA) were routinely used with 5–10 units of ligase in a 10 µl volume reaction. Polymerase chain reaction (PCR) was usually carried out 25 cycles, each with 1 minute denaturation at 94° C., 1 minute annealing at 60° C., and polymerization at 72° C. for 2 minutes per 1000 bases using the Pfu polymerase. For quantitative analysis, PCR was run 15–20 cycles, depending the gene expression levels, using the Taq polymerase (Promega, Madison, Wis.).

E. coli Transformation

For general cloning purpose, E. coli strain XL1-blue was routinely used as host cells for the transformation with plasmid DNAs. The competent E. coli cells were prepared in the laboratory and usually had an efficiency of $5 \times 10^{-6}$ to $10^{-7}$ colonies per µg control vector DNA. Three to five microliter of the ligation mixture was usually used to transform 100 µl of the competent E. coli cells. After incubation on ice for 20 minutes, the cell-DNA mixture was heat-shocked at 42° C. for 1 minute, and 1 ml of SOC medium was added. The mixture was then gently rotated at 37° C. for 1 hour to render the cells recovered from damage, and 50–300 µl was spread on LB plates containing an appropriate antibiotic. The plates were incubated at 37° C. overnight or until positive colonies were visible.

Plasmid Isolation and Purification

Vector DNA was isolated routinely by the alkaline-SDS method from E. coli culture. A 1 ml (for high copy number plasmid) or a 10 ml LB-ampicillin culture (for low copy number plasmid) was routinely prepared for the small scale purification of plasmid DNA. For the large scale purification, TB medium (Terrific broth, 47.6 grams of TB mix per liter, Difco, Detroit, USA) which gives higher plasmid DNA yields, instead of LB medium, was used. To prepare plasmid DNA for DNA sequencing and Agrobacterium transformation, those isolated by the alkaline-SDS method was further purified using the Plasmid Miniprep Kit II (Omega Biotek, Seoul, KOREA).

RNA Gel Blot Analysis

Seedlings were grown on MS-sucrose (2%) medium for 4.5 days in darkness and then transferred to FR light for the indicated times before harvesting under dim-green light. Total cellular RNA was extracted from whole seedlings using the RNeasy Miniprep kit (Qiagen, Valencia, Calif.). RNA gel blot analysis was performed as described (Soh et al., 1998).

Analysis of Arabidopsis Transgenic Lines

Full-length HFR1 was amplified by polymerase chain reaction (PCR) with HFR1 cDNA (Soh et al., 2000) using primers HFR1F4-2, 5'-CGA GAATTCATGTCGAATAATCAAGCTTTC-3' (SEQ ID NO: 3) and HFR1R8, 5'-CCTAATTTG GAATTCTTTTCTCTC-3' (SEQ ID NO: 4) and the mutant HFR1 (HFR1-ΔN105) lacking the N-terminal 105 amino acids was generated by PCR using primers, HFR1F5, 5'-CGAGAATTCATGAGAAACAAACATGAG-3' (SEQ ID NO: 5) and HFR1R8. The EcORI sites introduced are underlined and the ATG start codon introduced for HFR1-ΔN105 is shown in italic. The PCR products were digested with EcORI and then cloned into binary vector pNB96, obtained from Dr. Hong-Gil Nam (POSTECH, Republic of Korea), in which transgene is driven $^{35}$S dual promoter. The constructs were sequence verified. The resulting binary vector was introduced into Agrobacterium GV3101 and used to transform wild type Arabidopsis, Col or hfr1-201 mutant. More than 40 independent T1 transgenic plants were selected. Phenotypic analysis was performed with single T-DNA insertion lines of at least 20 independent lines.

Double Mutant Construction

To construct double mutants, we crossed HFR1-ΔN105 transgenic plants with light-signaling mutants and allowed the $F_1$ progeny to self-pollinate to produce the $F_2$ seeds. Basta-resistant plants were identified among the F2 seedlings and then grown for setting F3 seeds. The resulting F3 lines were tested for heterozygous basta-resistance and homozygous long-hypocotyl phenotypes under appropriate light conditions. From these, basta-resistant seedlings were selected and further grown to the F4 generation, and then plants were screened for homozygous basta-resistance. The resulting homozygous basta-resistant lines were designated as double mutants and used for phenotypic analysis.

REFERENCES

Ang, L. H., Chattopadhyay, S., Wei, N., Oyama, T., Okada, K., Batschauer, A., and Deng, X. W. (1998). Molecular interaction between COP1 and HY5 defines a regulatory switch for light control of Arabidopsis development. Mol. Cell 1, 213–222.

Ballesteros, M. L., Bolle, C., Lois, L. M., Moore, J. M., Vielle-Calzada, J. P., Grossniklaus, U., and Chua, N. H. (2001). LAF1, a MYB transcription activator for phytochrome A signaling. Genes Dev. 15, 2613–2625.

Benvenuto, G., Formiggini, F., Laflamme, P., Malakhov, M., and Bowler, C. (2002). The photomorphogenesis regulator DET1 binds the amino-terminal tail of histone $H_2B$ in a nucleosome context. Curr. Biol. 12, 1529–1534.

Büche, C., Poppe, C., Schäfer, E., and Kretsch, T. (2000). eid1: a new Arabidopsis mutant hypersensitive in phytochrome A-dependent high-irradiance responses. Plant Cell 12, 547–558.

Butler, W. L., Norris, K. H., Siegelman, H. W., and Hendricks, S. B. (1959). Detection, assay, and preliminary purification of the pigment controlling photoresponsive development of plants. Proc. Natl. Acad. Sci. USA 45, 1703–1708.

Chory, J., Peto, C., Feinbaum, R., Pratt, L., and Ausubel, F. (1989). Arabidopsis thaliana mutant that develops as a light-grown plant in the absence of light. Cell 58, 991–999.

Deng, X. W., Matsui, M., Wei, N., Wagner, D., Chu, A. M., Feldmann, K. A., and Quail, P. H. (1992). COP1, an Arabidopsis regulatory gene, encodes a protein with both a zinc-binding motif and a G homologous domain. Cell 71, 791–801.

Desnos, T., Puente, P., Whitelam, G. C., and Harberd, N. P. (2001). FHY1: a phytochrome A-specific signal transducer. Genes Dev. 15, 2980–2990.

Dieterle, M., Zhou, Y. C., Schäfer, E., Funk, M., and Kretsch, T. (2001). EID1, an F-box protein involved in phytochrome A-specific light signaling. Genes Dev. 15, 939–944.

Fairchild, C. D., Schumaker, M. A., and Quail, P. H. (2000). HFR1 encodes an atypical bHLH protein that acts in phytochrome A signal transduction. Genes Dev. 14, 2377–2391.

Fankhauser, C., and Chory, J. (1997). Light control of development. Annu. Rev. Cell Dev. Biol. 13, 203–229.

Fankhauser, C., and Chory, J. (2000). RSF1, an *Arabidopsis* locus implicated in phytochrome A signaling. Plant Physiol. 124, 39–45.

Furuya, M. (1993). Phytochromes-Their molecular species, gene families, and functions. Annu. Rev. Plant Physiol. Plant Mol. Biol. 44, 617–645.

Furuya, M., and Schäfer, E. (1996). Photoperception and signaling of induction reactions by different phytochromes. Trends Plant Sci. 1, 301–307.

Hardtke, C. S., Gohda, K., Osterlund, M. T., Oyama, T., Okada, K., and Deng, X.-W. (2000). HY5 stability and activity in *Arabidopsis* is regulated by phosphorylation in its COP1 binding domain. EMBO J. 19, 4997–5006.

Hoecker, U., and Quail, P. H. (2001). The phytochrome A-specific signaling intermediate SPA1 interacts directly with COP1, a constitutive repressor of light signaling in *Arabidopsis*. J. Biol. Chem. 276, 38173–38178.

Hoecker, U., Tepperman, J. M., and Quail, P. H. (1999). SPA1, a WD-repeat protein specific to phytochrome A signal transduction. Science 284, 496–499.

Huq, E. and Quail P. H. (2002). PIF4, a phytochrome-interacting bHLH factor, functions as a negative regulator of phytochrome B signaling in *Arabidopsis*. EMBO J. 21, 2441–2450.

Kim, Y. M., Woo, J. C., Song, P. S., and Soh, M. S. (2002b). HFR1, a phytochrome A-signaling component, acts in a separate pathway from HY5, downstream of COP1 in *Arabidopsis thaliana*. Plant J. 30, 711–719.

Kircher, S., Kozma-Bogner, L., Kim, L., Adam, E., Harter, K., Schäfer, E., and Nagy, F. (1999). Light quality-dependent nuclear import of the plant photoreceptors phytochrome A and B. Plant Cell 11, 1445–1456.

Lapko, V. N., Jiang, X. Y., Smith, D. L., and Song, P. S. (1997). Posttranslational modification of oat phytochrome A: Phosphorylation of a specific serine in a multiple serine cluster. Biochemistry 36, 10595–10599.

Lin, C. (2000) Plant blue-light receptors. Trends Plant Sci. 5, 337–342.

Nagy, F., and Schäfer, E. (2002). Phytochromes control photomorphogenesis by differentially regulated, interacting signaling pathways in higher plants. Annu. Rev. Plant Biol. 53, 329–55.

Neff, M. M., Fankhauser, C., and Chory, J. (2000). Light: an indicator of time and place. Genes Dev. 14, 257–271.

Okamoto, H., Matsui, M., and Deng, X. W. (2001). Overexpression of the heterotrimeric G protein a-subunit enhances phytochrome-mediated inhibition of hypocotyl elongation in *Arabidopsis*. Plant Cell 13, 1639–1651.

Osterlund, M. T., Hardtke, C. S., Wei, N., and Deng, X.-W. (2000). Targetted destabilization of HY5 during light-regulated development of *Arabidopsis*. Nature 405, 462–466.

Oyama, T., Shimura, Y., and Okada, K. (1997). The *Arabidopsis* HY5 gene encodes a bZIP protein that regulates stimulus-induced development of root and hypocotyl. Genes Dev. 11, 2983–2995.

Quail, P. H. (2002b). Phytochrome photosensory signaling networks. Nat. Rev. Mol. Cell Biol. 3, 85–93.

Quail, P. H., Boylan, M. T., Parks, B. M., Short, T. W., Xu, Y., and Wagner, D. (1995). Phytochromes: Photosensory perception and signal transduction. Science 268, 675–680.

Reed, J. W., Nagatani, A., Elich, T. D., Fagan, M., and Chory, J. (1994). Phytochrome A and phytochrome B have overlapping but distinct functions in *Arabidopsis* development. Plant Physiol. 104, 1139–1149.

Schroeder, D. F., Gahrtz, M., Maxwell, B. B., Cook, R. K., Kan, J. M., Alonso, J. M., Ecker, J. R., and Chory, J. (2002). De-etiolated 1 and damaged DNA binding protein 1 interact to regulate *Arabidopsis* photomorphogenesis. Curr. Biol. 12, 1462–1472.

Serino, G., Su, H., Peng, Z., Tsuge, T., Wei, N., Gu, H., and Deng, X. W. (2003). Characterization of the last subunit of the *Arabidopsis* COP9 signalosome: implications for the overall structure and origin of the complex. Plant Cell 15, 719–731.

Sharrock, R. A., and Quail, P. H. (1989). Novel phytochrome sequences in *Arabidopsis thaliana*: structure, evolution, and differential expression of a plant regulatory photoreceptor family. Genes Dev. 3, 1745–1757.

Shinomura, T., Nagatani, A., Hanzawa, H., Kubota, M., Watanabe, M., and Furuya, M. (1996). Action spectra for phytochrome A- and B-specific photoinhibition of seed germination in *Arabidopsis thaliana*. Proc. Natl. Acad. Sci. USA 93, 8129–8133.

Soh, M. S., Hong, S. H., Hanzawa, H., Furuya, M., and Nam, H. G. (1998). Genetic identification of FIN2, a far red light-specific signaling component of *Arabidopsis thaliana*. Plant J. 16, 411–419.

Soh, M. S., Kim, Y. M., Han, S. J., and Song, P. S. (2000). REP1, a basic helix-loop-helix protein, is required for a branch pathway of phytochrome A signaling in *Arabidopsis*. Plant Cell 12, 2061–2074.

Suzuki, G., Yanagawa, Y., Kwok, S. F., Matsui, M., and Deng, X. W. (2002). *Arabidopsis* COP10 is a ubiquitin-conjugating enzyme variant that acts together with COP1 and the COP9 signalosome in repressing photomorphogenesis. Genes Dev. 16, 554–559.

von Arnim, A. G., and Deng, X. W. (1994). Light inactivation of *Arabidopsis* photomorphogenic repressor COP1 involves a cell-specific regulation of its nucleocytoplasmic partitioning. Cell 79, 1035–1045.

Wei, N., and Deng, X. W. (1996). The role of the COP/DET/FUS genes in light control of *Arabidopsis* seedling development. Plant Physiol. 112, 871–878.

Wang, H., and Deng, X. W. (2002). *Arabidopsis* FHY3 defines a key phytochrome A signaling component directly interacting with its homologous partner FAR1. EMBO J. 21, 1339–1349.

Whitelam, G. C., and Devlin, P. F. (1997). Roles of different phytochromes in *Arabidopsis* photomorphogenesis. Plant Cell Environ. 20, 752–758.

Yamaguchi, R., Nakamura, M., Mochizuki, N., Kay, S. A., and Nagatani, A. (1999). Light-dependent translocation of a phytochrome B-GFP fusion protein to the nucleus in transgenic *Arabidopsis*. J. Cell Biol. 3, 437–445.

Yamamoto, Y. Y., Matsui, M., Ang, A.-H., and Deng, X.-W. (1998). Role of a COP1 interactive protein in mediating light-regulated gene expression in *Arabidopsis*. Plant Cell 10, 1083–1094.

Yamamoto, Y. Y., Deng, X.-W., and Matsui, M. (2001). CIP4, a new COP1 target, is a nucleus-localized positive regulator of *Arabidopsis* photomorphogenesis. Plant Cell 13, 399–411.

Yeh, K. C., and Lagarias, J. C. (1998). Eukaryotic phytochromes: light-regulated serine/threonine protein kinases with histidine kinase ancestry. Proc. Natl. Acad. Sci. USA 95, 13976–13981.

---

What is claimed is:

1. An isolated nucleic acid molecule comprising the nucleotide sequence of SEQ ID NO: 1.

2. An isolated nucleic acid molecule encoding an enzyme comprising the amino acid sequence of SEQ ID NO: 2.

* * * * *

SEQUENCE LISTING

<160> NUMBER OF SEQ ID NOS: 5

<210> SEQ ID NO 1
<211> LENGTH: 567
<212> TYPE: DNA
<213> ORGANISM: Arabidopsis sp.

<400> SEQUENCE: 1

```
atgagaaaca aacatgagaa ccccaaaaaa cgtcgtatcc aggtcttaag tagtgatgat     60
gaatcggagg agtttacaag agaagttcct tcagttactc gaaaaggttc caagagaaga    120
agaagagacg agaagatgag taataagatg cgtaagctac agcaactcgt acctaattgt    180
cacaagacgg acaaggtttc ggttctcgac aagaccatag agtatatgaa aaaccttcaa    240
cttcaacttc agatgatgtc aacagtgggg gtgaatcctt attttcttcc ggcgacatta    300
ggatttggaa tgcacaacca catgctgacg gcaatggctt cggctcacgg cctaaatccg    360
gcgaatcaca tgatgccatc gccgctaatt ccggcgttaa attggccatt accaccgttt    420
actaatattt cattcccaca ttcatctagt caatctctat ttcttacaac atcatcacca    480
gcttcttctc ctcagtctct tcacggtttg gttccttatt tcccaagttt cttggatttt    540
tcttcccatg cgatgagaag actatga                                        567
```

<210> SEQ ID NO 2
<211> LENGTH: 188
<212> TYPE: PRT
<213> ORGANISM: Arabidopsis sp.

<400> SEQUENCE: 2

```
Met Arg Asn Lys His Glu Asn Pro Lys Lys Arg Arg Ile Gln Val Leu
  1               5                  10                  15

Ser Ser Asp Asp Glu Ser Glu Glu Phe Thr Arg Glu Val Pro Ser Val
             20                  25                  30

Thr Arg Lys Gly Ser Lys Arg Arg Arg Asp Glu Lys Met Ser Asn
         35                  40                  45

Lys Met Arg Lys Leu Gln Gln Leu Val Pro Asn Cys His Lys Thr Asp
     50                  55                  60

Lys Val Ser Val Leu Asp Lys Thr Ile Glu Tyr Met Lys Asn Leu Gln
 65                  70                  75                  80

Leu Gln Leu Gln Met Met Ser Thr Val Gly Val Asn Pro Tyr Phe Leu
                 85                  90                  95

Pro Ala Thr Leu Gly Phe Gly Met His Asn His Met Leu Thr Ala Met
            100                 105                 110

Ala Ser Ala His Gly Leu Asn Pro Ala Asn His Met Met Pro Ser Pro
        115                 120                 125

Leu Ile Pro Ala Leu Asn Trp Pro Leu Pro Pro Phe Thr Asn Ile Ser
    130                 135                 140

Phe Pro His Ser Ser Ser Gln Ser Leu Phe Leu Thr Thr Ser Ser Pro
```

-continued

```
                 145                 150                 155                 160
Ala Ser Ser Pro Gln Ser Leu His Gly Leu Val Pro Tyr Phe Pro Ser
                     165                 170                 175

Phe Leu Asp Phe Ser Ser His Ala Met Arg Arg Leu
            180                 185

<210> SEQ ID NO 3
<211> LENGTH: 30
<212> TYPE: DNA
<213> ORGANISM: Artificial Sequence
<220> FEATURE:
<223> OTHER INFORMATION: HFR1F4-2 primer

<400> SEQUENCE: 3
cgagaattca tgtcgaataa tcaagctttc                                        30

<210> SEQ ID NO 4
<211> LENGTH: 24
<212> TYPE: DNA
<213> ORGANISM: Artificial Sequence
<220> FEATURE:
<223> OTHER INFORMATION: HFR1R8 primer

<400> SEQUENCE: 4
cctaatttgg aattcttttc tctc                                              24

<210> SEQ ID NO 5
<211> LENGTH: 27
<212> TYPE: DNA
<213> ORGANISM: Artificial Sequence
<220> FEATURE:
<223> OTHER INFORMATION: HFR1F5 primer

<400> SEQUENCE: 5
cgagaattca tgagaaacaa acatgag                                           27
```